United States Patent [19]

Lawford

[11] 4,355,106

[45] Oct. 19, 1982

[54] CONTINUOUS PROCESS FOR THE PRODUCTION OF GELABLE EXOPOLYSACCHARIDE

[75] Inventor: Hugh G. Lawford, Mississauga, Canada

[73] Assignee: George Weston Limited, Toronto, Canada

[21] Appl. No.: 223,960

[22] Filed: Jan. 12, 1981

[51] Int. Cl.$^3$ .......................... C12P 19/04; C12R 1/05
[52] U.S. Cl. .................................. 435/101; 435/813; 435/819; 435/829
[58] Field of Search ............... 435/101, 104, 813, 819, 435/829

[56] References Cited

U.S. PATENT DOCUMENTS

| | | | |
|---|---|---|---|
| 3,015,612 | 1/1962 | Pirt et al. ............................ | 435/813 |
| 3,328,262 | 6/1967 | Lindblom et al. .................. | 435/813 |
| 3,754,925 | 8/1973 | Kimura et al. ...................... | 435/101 |
| 4,218,538 | 8/1980 | Church ................................ | 435/101 |
| 4,298,725 | 11/1981 | Williams et al. .................... | 435/101 |

*Primary Examiner*—Esther M. Kepplinger

*Attorney, Agent, or Firm*—Rogers, Bereskin & Parr

[57] ABSTRACT

The present invention is directed to a two-stage continuous process for the production of a gelable curdlan-type exopolysaccharide. In the first stage a stable, curdlan-producing strain of microorganism such as *Alcaligenes faecalis* var. *myxogenes* ATCC 31749 and ATCC 31750, is grown aerobically in an aerated, agitated culture medium containing assimilable carbon, nutrients and organic salts. The amount of nitrogen in the first stage is so limited that the effluent therefrom contains substantially no inorganic nitrogen. The effluent is introduced into a second stage in a constant volume fermenter wherein it is mixed with a nitrogen-free carbohydrate. The resultant mixture is aerated and mixed at pH 5.5 to 6.5 at a temperature of from 25° to 35° C., the volume and dilution rate in the reactor being selected so that the residence time of the microorganism in the fermenter does not exceed an equivalent to the maximum length of time during which the activity of a batch culture of the microorganism with respect to product synthesis is maximal. The product is subsequently isolated.

5 Claims, No Drawings

CONTINUOUS PROCESS FOR THE PRODUCTION OF GELABLE EXOPOLYSACCHARIDE

This invention relates to a microbial process whereby a gelable extracellular microbial polysaccharide, also known as an exopolysaccharide, can be produced continuously by means of a stable, curdlan-producing strain of microorganism.

Exopolysaccharides have found diverse applications in industry, principally the food industry and the petroleum industry. In the food industry they replace or extend natural plant gums as stabilizers, emulsifiers and thickeners. In the petroleum industry they have been used in both drilling and oil recovery operations. Many different microorganisms are known which produce exopolysaccharides. The chemical composition and structure of the exopolysaccharide are relatively species specific, i.e. they are dependent upon the strain of microorganism used in its production. With certain microorganisms, exopolysaccharide synthesis accompanies growth but with others exopolysaccharide production occurs primarily during the non-growing or resting stage.

It is known that strains of the bacterium *Agrobacterium radiobacter* and the bacterium *Alcaligenes faecalis* var. *myxogenes* synthesize an extracellular, neutral water-insoluble $\beta$-1,3-glucan homopolymer. This is described in U.S. Pat. No. 3,754,925 which issued on Aug. 28, 1973 to Kimura et al. The unique physicochemical properties of this homopolymer, which is referred to as "a curdlan-type" polymer make it particularly attractive to the food industry as a thickener or bodying agent in certain edible products. The property which is most interesting is its irreversible thermo-gelling property. In the process described in the above-mentioned patent, the exopolysaccharide production occurred after growth ceased in a nitrogen deficient medium.

The prior art process normally employed for curdlan-type polymer production is a batch process requiring approximately a four-day fermentation to give a product concentration of 5% (w/v). This is shown in the publication by T. Harada (1977). "*Production, Properties and Application of Curdlan., Extracellular Microbiol Polysaccharides*" ACS Symposium Series Number 45, Am. Chem. Soc., Washington, U.S.A. pp 265–283. It is well known that a continuous process has many advantages as compared to batch processes. Attempts have been made by others to produce microbial exopolysaccharides in single-stage continuous fermentations. However, only those microorganisms which are known to produce expolysaccharides during growth are amenable to single-stage continuous culture. Examples of such processes are the syntheses of bacterial alginate by bacteria of the genus Azotobacter and xanthan gum by Xanthomonas.

One of the limitations of the single-stage continuous production process is that, in order to achieve relatively efficient utilization of the carbohydrate feedstock, the economic dilution rate is often much slower than the maximum specific growth rate of the microorganism. A more serious limitation to continuous operation relates to apparent deterioration of a continuous culture with respect to exopolysaccharide production. The report of Silman and Rogovin (1972) Biotechnol. Bioeng 14, 23–31, indicates that the ability of *Xanthomonas campestris* to produce xanthan gum is rapidly lost during continuous culture in a single-stage chemostat.

For continuous fermentation, the total operating time is often referred to in terms of the number of culture turnovers. A culture turnover occurs during a time interval equal in value to the reciprocal of the dilution rate.

In the above-identified report, it was stated that xanthan production by Xanthamonas ceases in a single-stage continuous fermentation after 6.5 to 8.7 turnovers. Attempts have been made to solve the problem of culture instability or deterioration by employing a threestage continuous process for xanthan production by Xanthamonas. This process is described in U.S. Pat. No. 3,328,262 which issued to Lindblom et al on June 27, 1967. However, this multi-stage system was only operated over a 95 hour period which, for that particular system, represented only three turnovers.

Tests have shown that single-stage continuous culture of curdlan-producing bacteria is not accompanied by continuous exopolysaccharide production.

It has now been found that the exopolysaccharides referred to as a curdlan-type exopolysaccharide can be produced continuously in a two-stage process using a stable-curdlan-producing microorganism wherein the polymer biosynthesis is not dependent upon, nor associated with, growth.

Accordingly, the present invention is directed to a two-stage continuous process for the production of a gelable curdlan-type exopolysaccharide in which (1) a stable, curdlan-producing strain of microorganism is grown aerobically under conditions of continuous culture at pH 6 to 8 and at a temperature of from 22° to 37° C. in an agitated culture medium containing assimilable carbon, nutrients, and inorganic salts and also containing assimilable nitrogen in an amount so limited that the effluent from the first stage contains substantially no inorganic nitrogen, and continuously (2) introducing the effluent into a constant volume fermenter wherein it is mixed with a nitrogen-free carbohydrate, the resultant mixture is aerated and mixed at pH 5.5 to 6.5 and a temperature of from 25° to 35° C., the volume and dilution rate in the fermenter being selected so that the residence time of the microorganism in the fermenter does not exceed an equivalent to the maximum length of time during which the activity of a batch culture of the microorganism with respect to product synthesis is maximal, and subsequently isolating the product.

The preferred stable, curdlan-producing strains of microorganisms for use in the present invention are of the species *Alcaligenes faecalis* var. *myxogenes*. These strains avoid the problems or constraints referred to above. The growth limiting nutrient in the culture medium in the first stage of this synthesis is nitrogen. The amount of assimilable nitrogen in the culture medium defines the steady-state level of biomass being continuously produced in the first stage and the rate at which the medium is pumped into the first constant-volume fermenter establishes the growth rate of the microorganism or a rate at which biomass is generated in the system. The biomass effluent from the first fermenter contains a negligible amount of nitrogen so that growth is not possible in the second-stage fermenter which is also maintained at a constant volume. Tests have shown that this use of a two-stage process with a medium of defined composition permits continuous production of curdlan-type polysaccharide in good yield.

When the particular uracil-requiring auxotrophic mutant strain of *Alcaligenes faecalis* var. *myxogenes*

(ATCC 21680) which is referred to in the above-mentioned U.S. Pat. No. 3,754,925 is cultured continuously under conditions of nitrogen-limitation and high dilution rate it is replaced spontaneously by a variant species of *A. faecalis* var. *myxogenes which characteristically lacks an absolute requirement of uracil for growth. For this reason A. faecalis var. myxogenes (ATCC* 21680) is not compatible with continuous culture over prolonged periods in a nitrogen-limited growth environment specified for the first stage of the two-stage process of the present invention.

In the first stage of the process of this invention, a stable curdlan-type exopolysaccharide producing microorganism is grown aerobically in a chemically defined medium in a chemostat by the prior art process of continuous culture. The culture medium contains assimilable carbon and nitrogen together with other nutrients and inorganic salts required by the microorganism for its growth. The growth limiting element in the culture medium is nitrogen, all other essential growth elements being present in excess. The temperature is maintained constant in the range of from 22° to 37° C. and the pH is kept constant in the range of 6 to 8. It will be appreciated that the optimum temperature is 30° C. and pH is 7. The culture is thoroughly mixed and aerated. The constant volume continuous fermenter of the first stage is operated at a dilution rate so as to achieve maximum biomass productivity with almost negligible inorganic nitrogen in the fermenter effluent.

The effluent from the first continuous fermenter is fed directly to a second stage constant volume fermenter which constitutes the second stage of the continuous process in which the biomass synthesizes the desired exopolysaccharide. A nitrogen-free solution of carbohydrate feedstock, from which the microorganism can synthesize the desired polysaccharide product, is fed continuously to the second stage fermenter. The volume of the second stage is kept constant. The volume and the dilution rate are fixed such that the residence time of the organism in the second stage is equivalent to the maximum length of time during which the activity of a batch culture with respect to product synthesis is maximal. The carbohydrate feedstock is added at a rate which does not largely exceed the rate at which it can be utilized for polymer biosynthesis. The pH of the second stage is kept constant in the range of 5.5 to 6.5 and the temperature is maintained in the range of from 25° to 35° C. The optimum pH is 5.9 and the optimum temperature is about 30° C. Once again, the second stage of the process is aerated with thorough mixing.

Product recovery from the effluent of the second stage is achieved according to known methods of alkali treatment and centrifugation followed by neutralization of the supernatant to form a gel (H. Harada et al (1968), J. Ferment.Technol.46, 679–684).

The carbohydrate feedstock for use in either stage 1 or stage 2 of the process of the present invention, i.e. the source of assimilable carbon in stage (1) and of nitrogen-free carbohydrate in stage (2), can be sucrose, maltose, lactose, fructose, galactose, xylose, glucose or a hydrolysate of starch.

The preferred stable, curdlan-producing strains of microorganisms for use in the process of the present invention are *Alcaligenes faecalis* var. *myxogenes* ATCC 31749, *Alcaligenes faecalis* var. *myxogenes* ATCC 31750. The descriptions of these microorganisms follows.

DESCRIPTION OF THE MICROORGANISMS

I. *Alcaligenes faecalis* var *myxogenes* ATCC 31749

This strain has been deposited with the American Type Culture Collection under the accession number ATCC 31749. This strain was isolated as a spontaneous mutant of the uracil-requiring auxotrophic parent ATCC 21680. This strain displays the following physiological and biochemical characteristics according to classical bacteriological tests:
1. Optimum temperature of growth: 30° C.
2. Optimum pH for growth: 7
3. Relation to free oxygen: aerobic
4. Gelatin: not liquified
5. Litmus milk: slightly alkaline; not coagulated; no reduction
6. Indole: not produced
7. Hydrogen sulphide: not produced
8. Nitrates: reduced to nitrites
9. Methyl Red test: negative
10. Voges-Proskauer test: negative
11. Starch: not hydrolyzed
12. Catalase: positive
13. Oxidase: weak
14. Citric acid: utilized
15. Ammonium salts, nitrates and urea are utilized as sole nitrogen sources
16. Uracil: not required for growth
17. Suitable sole carbon sources: ethylene glycol, lactose, maltose, sucrose, glucose, galactose, mannose, fructose, starch hydrolysates, raffinose, arabinose, xylose, ribose, glycerol, sorbitol, mannitol and potassium salts of the organic acids succinate and fumarate.
18. Gram Stain: negative This strain is not substantially different either morphologically or physiologically from its auxotrophic parent ATCC 21680. The distinguishing trait is that the variant ATCC 31749 does not exhibit a requirement for exogenous uracil for growth.

II. *Alcaligenes faecalis* var *myxogenes* ATCC 31750

This strain has been deposited with the American Type Culture Collection under the accession number ATCC 31750. This strain arose as a spontaneous variant of the parent ATCC 31749 described above. This strain exhibits physiological characteristics and responds to typical biochemical and bacteriological tests in an identical manner to its parent strain. This strain is distinguished from ATCC 31749 and recognized by its colony morphology in the following manner.
1. When plated on glucose-inorganic salts agar, colonies of this strain ATCC 31750 appear raised, rough with a dry, wrinkled texture in contrast to those of its parent which typically appear circular, convex, smooth and glistening.
2. In broth culture it forms a sediment with no pellicle formation or growth throughout, while the parent strain has a moderate pellicle and weak growth with a small sediment.
3. Both colony types are cream coloured, the rough one being slightly whiter.

EXAMPLE 1

The continuous fermenter of the first stage was a small-scale chemostat (New Brunswick Scientific Co., model BioFlo C30) with a working volume of 340 ml. The chemical composition of the mineral salts culture medium was as follows: $KH_2PO_4$ 0.174% (w/v); $Na_2SO_4.10H_2O$ 0.37%; $K_2HPO_4$ 0.049%, $NH_4Cl$ 0.21%;

MgCl$_2$.6H$_2$O 0.025%; FeCl$_3$.6H$_2$O 0.0024%; MnCl$_2$.4H$_2$O 0.001%; CaCl$_2$.2H$_2$O 0.0015%; citric acid.H$_2$O 0.021%; polypropylene glycol (2025) as antifoaming agent 0.01% (v/v); uracil 0.01% (w/v) and D-glucose 0.87%. Separately sterilized solutions of glucose, uracil and mineral salts were added aseptically to a sterile culture medium reservoir vessel which contained a magnetic stir-bar for continuous agitation of the culture medium. The culture medium was metered from the reservoir vessel by means of a peristaltic pump and fed to the chemostat at a fixed rate of 84 ml/hr. The chemostat was inoculated with *Alcaligenes faecalis* var *myxogenes ATCC* 31749. The pH of the continuous culture was maintained at pH 7 by means of an automatic pH controller (New Brunswick Scientific model pH-40), the titrant being 3 N KOH. The temperature was kept constant at 30° C. Mixing was accomplished by means of a magnetically driven impeller operating at 600 RPM. The culture was ventilated by filter-sterilized air at a rate of 1.4 v/v/min. At a dilution rate of 0.25 hr$^{-1}$, the steady-state biomass concentration in the chemostat was 4 g D.W./L. The concentration of inorganic nitrogen and glucose in the fermenter effluent were 0.0006% and 0.1% respectively.

The effluent from the first continuous fermenter (stage I) was fed directly to a second fermenter (New Brunswick Scientific Co; Model MF114). The working volume of the second continuous fermenter (stage II) was kept constant at 6 L by means of an exit weir device coupled to a continuously operating peristaltic pump. A sterile glucose solution (6.2% w/v) was pumped to the stage II fermenter from a holding tank at a rate of 34 ml/hr.

Before coupling the first and second stage fermenters the start-up procedure for the stage II fermenter proceeded as follows: the 14 L fermenter vessel was charged with about 6 L of sterile culture medium. The chemical composition of the culture medium was as previously described with two exceptions: the concentration of the sole nitrogen source (NH$_4$Cl) was 0.147% and the carbon source (glucose) was 0.68%. The fermenter was inoculated with a seed culture of *A. faecalis* var *myxogenes* (ATCC 31749) and grown aerobically as a batchculture. The temperature was 30° C. and the pH was maintained at pH 7. At stationary-phase of growth the biomass concentration was 2.8 g. D.W./L and the residual glucose concentration was 0.04% while the NH$_4$Cl concentration was negligible. The pH of the stationary-phase culture was adjusted with 4 N HCl to 6.0 before coupling the effluent stream of the first stage chemostat to the second stage fermenter and starting the glucose feed to the second stage reactor to initiate exopolysaccharide biosynthesis.

Operating parameters for the second stage continuous fermenter were as follows: temperature was maintained at 30° C., the pH was kept constant in the range 5.9–6.1. The culture was ventilated with filter-sterilized air at a rate of 0.33 v/v/min and stirring was at 300 RPM. Steady-state was achieved after a period of 2 days from commencing flow through the second stage fermenter. At a dilution rate of 0.02 hr$^{-1}$ (mean residence time=50 hr) the following steady-state concentrations were recorded: biomass, 2.8 g D.W/L; glucose, 0.09% and curdlan-type exopolysaccharide, 0.7%.

Product recovery is accomplished by adding equal volumes of culture broth and 1 N NaOH. This is stirred at room temperature for 15 minutes followed by centrifugation at 12,100 xg for 10 minutes to remove the cells. If the solution is thick it may be diluted further with 0.5 N NaOH before it is centrifuged. The supernatant is then neutralized with 4 N HCl and centrifuged again at 12,100 xg for 10 minutes. The polysaccharide appears as a "gel-like" pellet. This pellet is then washed three times with distilled water, frozen with liquid N$_2$ and lyophilized.

The yield of exopolysaccharide product recovered by this procedure relative to glucose feedstock in this continuous process is 42%.

The $\beta$-1,3-glucan homopolymer obtained in this process exhibits all the physiochemical properties including thermal gelation consistent with it being a curdlan-type extracellular polysaccharide, This two stage continuous production process was operated as described above for a period of 21 days without any detectable deterioration in the ability of the biomass produced in the first stage to produce the desired exopolysaccharide product.

I claim:

1. A two-stage continuous process for the production of a gelable curdlan-type exopolysaccharide in which
   (1) a stable, curdlan-producing strain of microorganism is grown aerobically under conditions of continuous culture at pH 6 to 8 and at a temperature of from 22° to 37° C. in an aerated, agitated culture medium containing assimilable carbon, nutrients, and inorganic salts and also containing nitrogen in an amount so limited that the effluent from the first stage contains substantially no inorganic nitrogen, and continuously
   (2) introducing the effluent into a constant volume fermenter wherein it is mixed with a nitrogen-free carbohydrate, the resultant mixture is aerated and mixed at pH 5.5. to 6.5 at a temperature of from 25° to 35° C., the volume and dilution rate in the reactor being selected so that the residence time of the microorganism in the fermenter does not exceed an equivalent to the maximum length of time during which the activity of a batch culture of the microorganism with respect to product synthesis is maximal, and subsequently isolating the product.

2. A process as claimed in claim 1 in which the microorganism is *Alcaligenes faecalis* var. *myxogenes* ATCC 31749.

3. A process as claimed in claim 1 in which microorganism is *Alcaligenes faecalis* var. *myxogenes* ATCC 31750.

4. A process as claimed in claim 1, claim 2 or claim 3 in which stage one is carried out at a pH of 7 at a temperature of 30° C. and the second stage is carried out at a pH of 5.9 and a temperature of 30° C.

5. A process as claimed in claim 1, claim 2 or claim 3 in which the assimilable carbon for stage (1) and nitrogen-free carbohydrate in stage (2) are present in the form of at least one member of the group of sucrose, maltose, lactose, fructose, galactose, xylose, glucose and hydrolysates of starch.

* * * * *